United States Patent [19]

Dettbarn et al.

[11] 4,403,986
[45] Sep. 13, 1983

[54] NEEDLE-LESS INJECTION INSTRUMENT

[75] Inventors: Hans-Jürgen Dettbarn, Marburg; Josef Zimmermann, Sulzbach, both of Fed. Rep. of Germany

[73] Assignee: Hoechst Aktiengesellschaft, Frankfurt am Main, Fed. Rep. of Germany

[21] Appl. No.: 368,157

[22] Filed: Apr. 14, 1982

[30] Foreign Application Priority Data

Apr. 16, 1981 [DE] Fed. Rep. of Germany ....... 3115377

[51] Int. Cl.³ .............................................. A61M 5/30
[52] U.S. Cl. ..................................................... 604/70
[58] Field of Search ........................ 604/70, 71, 68, 73, 604/48, 131, 181, 140–150

[56] References Cited

U.S. PATENT DOCUMENTS 2,928,390  3/1960  Venditty et al. ...................... 604/70
3,292,622  12/1966 Banker ................................. 604/70
3,526,225  9/1970  Isobe ................................... 604/71
3,805,783  4/1974  Ismach ................................. 604/71
3,945,379  3/1976  Pritz et al. ........................... 604/70

Primary Examiner—John D. Yasko
Attorney, Agent, or Firm—Curtis, Morris & Safford

[57] ABSTRACT

In this injection instrument, the piston pump (A) is connected to a drive motor (B), the working piston (5) of which is arranged displaceably in a cylindrical bore (6) of the motor housing (1).

To ensure that, in the case of different piston strokes of the piston pump (A), the pump pressure remains the same and, on the other hand, injection can be effected only when the instrument rests on the skin, the drive motor (B) is provided with a spring housing (3) in which is located a working spring (2) which is supported at one end on a supporting face (18) in the spring housing (3) and at the other end on an end face (9) in the motor housing (1) and is guided by a part of the working piston (5) designed as a piston rod (4). To retain the tensioned working piston (5), the spring housing (3) is provided with a recess (11) for a pawl (10) which is supported by a bolt (13) arranged displaceably in the motor housing (1).

6 Claims, 3 Drawing Figures

NEEDLE-LESS INJECTION INSTRUMENT

The invention relates to a needle-less injection instrument with a piston pump for the medium to be injected, which is connected to a drive motor, the working piston of which is arranged displaceably in a cylindrical bore of the motor housing.

A needle-less injection instrument according to the pre-characterizing clause of patent claim 1 is known form U.S. Pat. No. 3,526,225, and in this the drive motor consists of a piston with a short piston rod, a spring and an adjustable guide for the spring. The spring is compressed hydraulically and retained in this position by the hydraulic fluid. The guide for the spring engages with a spindle, by which the distance between the free end face of the guide and the end face of the piston rod and consequently the stroke of the piston rod can be adjusted. A disadvantage of this is that the compressed spring has to be retained in its position by the hydraulic fluid and has to be firmly clenched to release the trigger lever, so that the hydraulic fluid can flow out from the hydraulic cylinder without a braking effect for the spring.

The invention is intended to remedy this. The invention, as defined in the claims, achieves the object by an arrangement, wherein the drive motor has a spring housing which is secured against rotation and in which is located a working spring which is supported at one end on a supporting face in the spring housing and at the other end on an end face limiting the bore in the motor housing and is guided by a part of the working piston which is designed as a piston rod and which is provided with a crank and a thread engaging with a corresponding thread in the spring housing.

The spring housing is provided with a recess for receiving a pawl which is located in the motor housing and which is supported by a bolt arranged displaceably in the motor housing. The bolt is provided with a conical part onto which the pawl is pushed when it engages into the recess of the spring housing. One end of the bolt is connected to an operating element for the drive motor. The other end freely movable in the motor housing is provided with a stud which is guided in a bearing fastened in the motor housing and which carries a spring supported on the bearing and on the free end of the stud.

The advantages achieved by means of the invention are to be seen essentially in the fact that it guarantees that the working piston and consequently the piston pump can be set in motion, that is to say the shot fired, only when the injection instrument is pressed, for example, onto the skin, that is to say onto the place where injection is to be carried out. After release, the shot is given automatically, and injection takes place with skin contact. Operating errors are therefore prevented.

The invention is explained in more detail below with reference to drawings which illustrate only one form of construction and in which.

Figure 1:
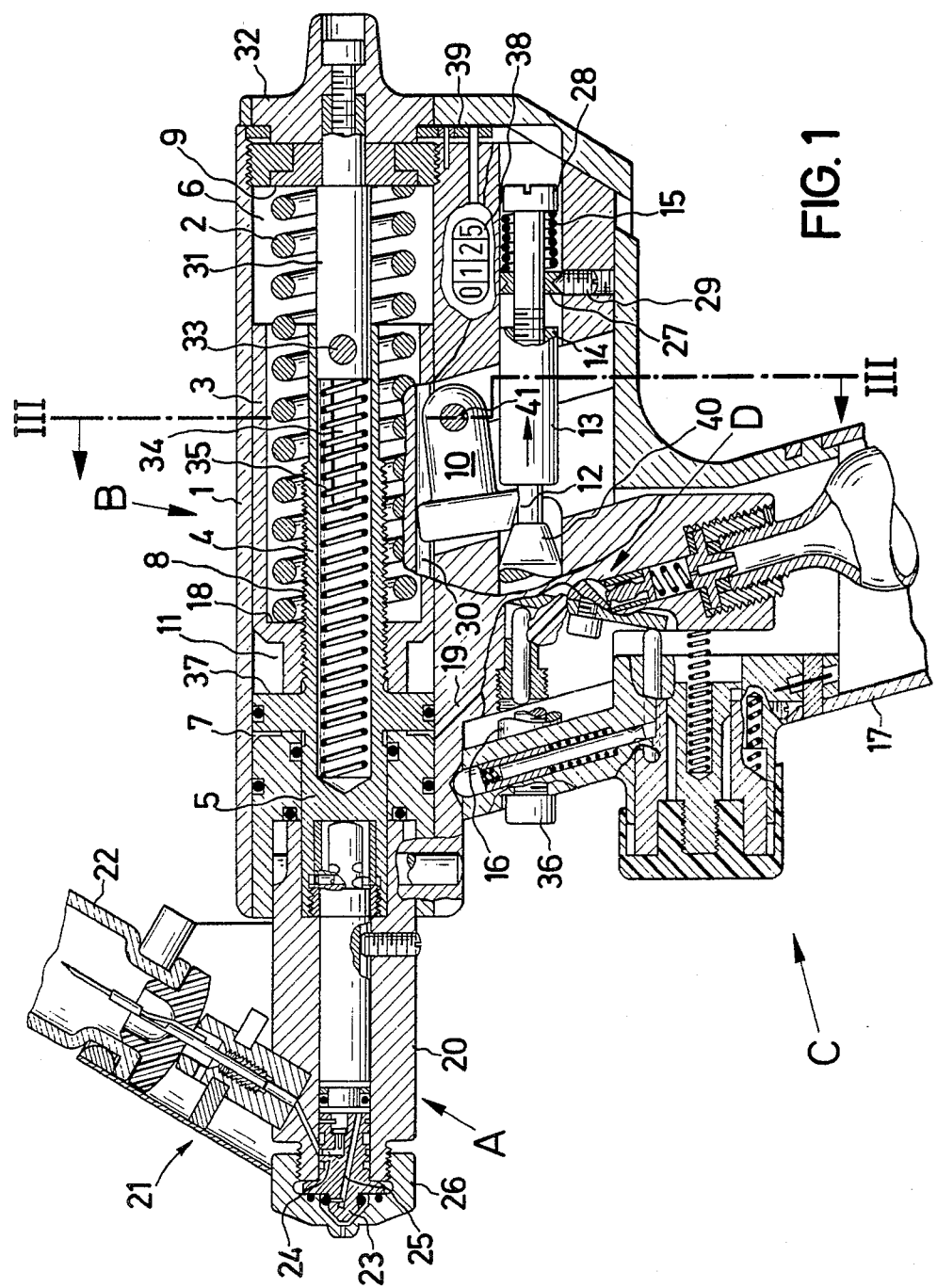
FIG. 1 shows a side view of the injection instrument, partially in section and in sections along various planes, in the closed-off state.
Figure 2:
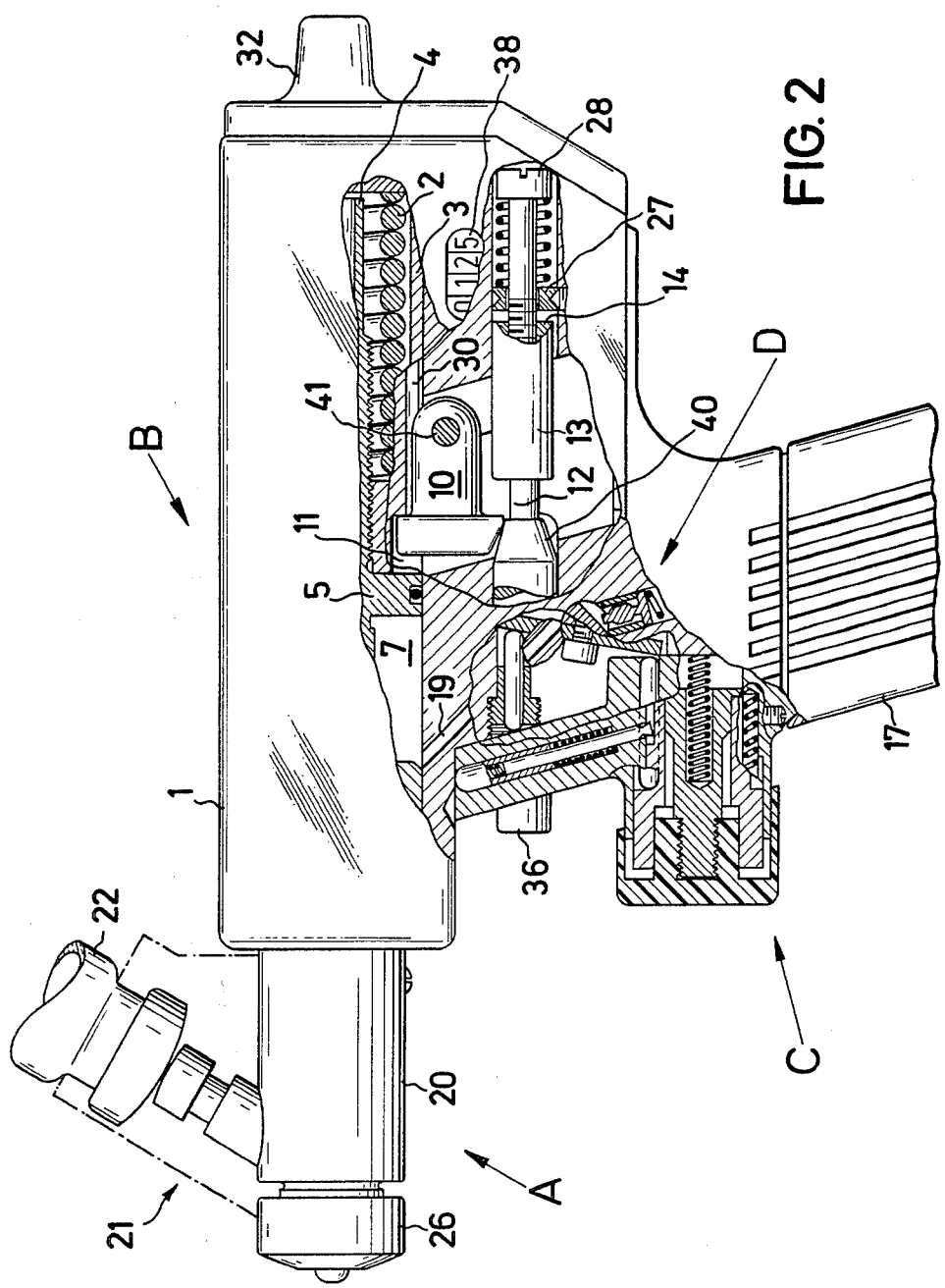
FIG. 2 shows a side view of the injection instrument, partially in section and in sections along various planes, in the loaded state.
Figure 3:
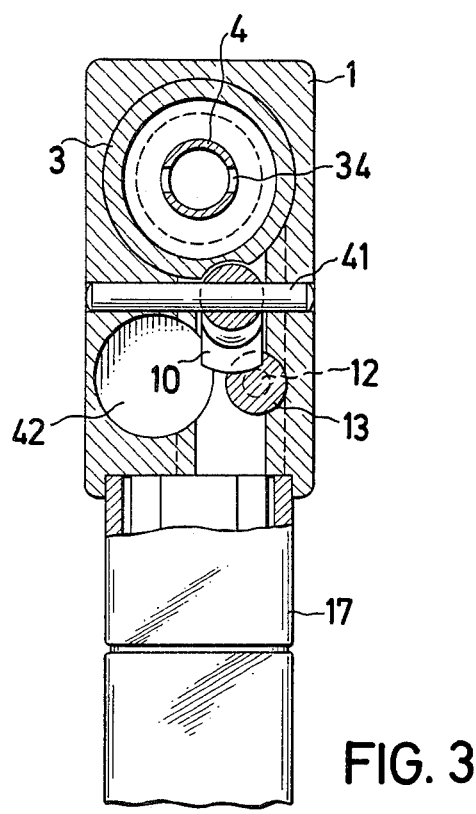
FIG. 3 shows the section along the line III—III in FIG. 1.

The needle-less injection instrument consists essentially of a piston pump (A) for the medium to be injected, which is connected releasably to a drive motor (B). The housing (20) of the piston pump (A) carries a device (21) for receiving a vessel (22) for the medium to be injected, and a valve body (23) with an inlet channel (24) and an outlet channel (25) for the medium to be injected, and a nozzle (26). The working piston (5) of the drive motor (B) is located in a cylindrical bore (6) of the motor housing (1). The drive motor (B) has a spring housing (3) which is secured against rotation by a groove (30) and which is provided with a thread. This engages with a corresponding thread (8) which the part of the working piston (5) designed as a piston rod (4) possesses. The piston rod (4) is connected by means of a crank consisting, for example, of a driver (31) to a rotary knob (32) accessible from outside. The driver (31) has a peg (33) which is guided in a recess (34) in the piston rod (4). The spring (35) serves for assembling the driver (31). By rotating the rotary knob (32) the distance between the working piston (5) and the shoulder (37) of the spring housing is adjusted, the stroke of the working piston (5) and consequently also that of the coupled piston pump (A) being changed. During this time, however, the maximum pressure of the working spring (2) remains unchanged, so that, in the case of a different dosage of the vaccine, the spring force is not changed. The rotary knob (32) is coupled to a counter (38), if appropriate via a suitable gear (39) which indicates the set dosage quantity. The counter is located in a recess (42) (FIG. 3).

Located in the spring housing (3) is a working spring (2) which is supported at one end on a supporting face (18) in the spring housing (3) and at the other end on an end face (9) limiting the bore (6) in the motor housing (1). The spring housing (3) is also provided with a recess (11) for receiving a pawl (10) which is arranged rotatably about the axle pin (41) in the motor housing (1) and which is supported by a bolt (13). The bolt (13) is arranged axially displaceably in the motor housing (1) and, as soon as the working spring (2) is tensioned, is drawn in the direction of the arrow at the free end (14) by a pre-stressed spring (15). As a result, the pawl which rested on the shoulder (12) of the bolt (13) is lifted by the conical part (40) of the bolt (13) and is pushed into the recess (11) of the spring housing (3). The spring (15) is supported on a bearing ring (27) for the bolt (13) and on the free end of a stud (28), for example the head of a screw, which the free end (14) of the bolt (13) possesses. The bearing ring (27) is retained in the motor housing (1) by means of a screw (29). The end (16) of the bolt (13) is connected firmly, for example by means of a screw (36), to an operating element (C), for example a grip (17), which can thus likewise be displaced relative to the motor housing (1).

To tension the working spring (2), the space (7) is filled with a pressure medium, for example with pressure gas, which is supplied via a channel (19). The pressure force of the working piston (5) acts via the spring housing (3) on the working spring (2) and compresses the latter until the spring housing (3) rests against the end face (9). The pawl (10) can now engage into the recess (11) of the spring housing (3). The space (7) filled with pressure medium is emptied via a channel not shown.

To relax the working spring (2), the grip (17) is pushed, as a result of pressure by the nozzle (26) on the subject to be injected, against the force of the spring

(15) in the direction of the subject. At the same time, the bolt (13) is carried with it, as a result of which the pawl (10) loses its support; the working spring (2) can relax.

(D) indicates the control for the pressure medium.

We claim:

1. A needle-less injection instrument with a piston pump for the medium to be injected, which is connected to a drive motor, the working piston of which is arranged displaceably in a cylindrical bore of the motor housing, wherein the drive motor (B) has a spring housing (3) which is secured against rotation and in which is located a working spring (2) which is supported at one end on a supporting face (18) in the spring housing (3) and at the other end on an end face (9) limiting the bore (6) in the motor housing (1) and is guided by a part of the working piston (5) which is designed as a piston rod (4) and which is provided with a crank and a thread (8) engaging with a corresponding thread in the spring housing (3).

2. The injection instrument as claimed in claim 1, wherein the spring housing (3) is provided with a recess (11) for receiving a pawl (10) which is located in the motor housing (1) and which is supported by a bolt (13) arranged displaceably in the motor housing (1).

3. The injection instrument as claimed in claim 2, wherein the bolt (13) is provided with a conical part (40) onto which the pawl (10) is pushed when it engages into the recess (11) of the spring housing (3).

4. The injection instrument as claimed in claim 2 or 3, wherein the end (16) of the bolt (13) is connected to an operating element (C) for the drive motor (B).

5. The injection instrument as claimed in claim 2, 3 or 4, wherein the end (14) of the bolt (13) is provided with a stud (28) which is guided in a bearing (27) fastened in the motor housing (1) and which carries a spring (15) supported on the bearing and on the free end of the stud (28).

6. The injection instrument as claimed in claim 1, wherein the crank is connected to a counter (38) for indicating the stroke of the piston pump.

* * * * *